United States Patent [19]
Hoover et al.

[11] Patent Number: 6,089,715
[45] Date of Patent: Jul. 18, 2000

[54] AUTOMATED PHOTOREFRACTIVE SCREENING

[75] Inventors: Adam Hoover, San Diego; Stuart Brown; Barbara Brody, both of La Jolla; Dirk-Uwe Bartsch, Del Mar; David Granet, San Diego, all of Calif.

[73] Assignee: EyeDx, Inc., San Diego, Calif.

[21] Appl. No.: 09/173,571

[22] Filed: Oct. 15, 1998

Related U.S. Application Data

[60] Provisional application No. 60/062,072, Oct. 15, 1997.

[51] Int. Cl.$^7$ .................................................. A61B 3/10
[52] U.S. Cl. ............................................................. 351/221
[58] Field of Search .................................... 351/204, 206, 351/208, 209, 210, 221; 600/558; 396/51

[56] References Cited

U.S. PATENT DOCUMENTS

| | | |
|---|---|---|
| 4,950,069 | 8/1990 | Hutchinson .............................. 351/210 |
| 5,218,387 | 6/1993 | Ueno et al. . |
| 5,355,895 | 10/1994 | Hay . |
| 5,632,282 | 5/1997 | Hay et al. . |

*Primary Examiner*—George Manuel
*Attorney, Agent, or Firm*—Fish & Richardson P.C.

[57] ABSTRACT

A system and method for locating and modeling eyes in imagery for automated photorefractive screening. The invention includes a digital camera having a lens-mounted flash for obtaining a digital image of the face of an individual, and a suitably programmed processor, such as a general purpose digital computer, for locating an eye of the individual in the digital image, modeling structures in the eye, analyzing the digitized eyes of the individual for eye disease, and providing a recommendation for treatment. In one aspect, the invention includes a system and method for locating a patient's eyes in a digital image that includes each eye as illuminated by a near-axis flash, including automatically finding light reflexes in the digital images as indicative of the location of each eye. Automatically finding light reflexes includes analyzing such light reflexes to determine possible pupil and sclera borders. The invention further includes automatically fitting a corresponding model to such possible pupil and sclera borders, analyzing the model of each eye to determine possible abnormalities in each eye; and outputting a possible diagnosis for each eye based on such analyzing. Other aspects of the invention include measuring retinal reflexes and corneal reflexes from the indicated eye models as an indicator of anomalies in the patient's eyes, and generating a digital image of each of a patient's eyes with a camera having a flash positioned near to a center line of a lens of the camera so as to generate images with bright, sharp light reflexes.

31 Claims, 7 Drawing Sheets

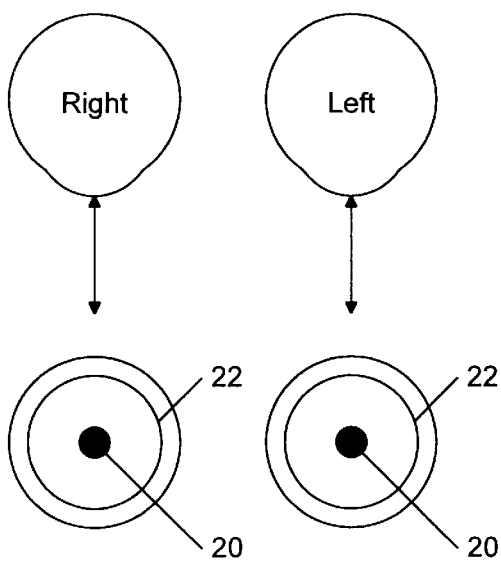
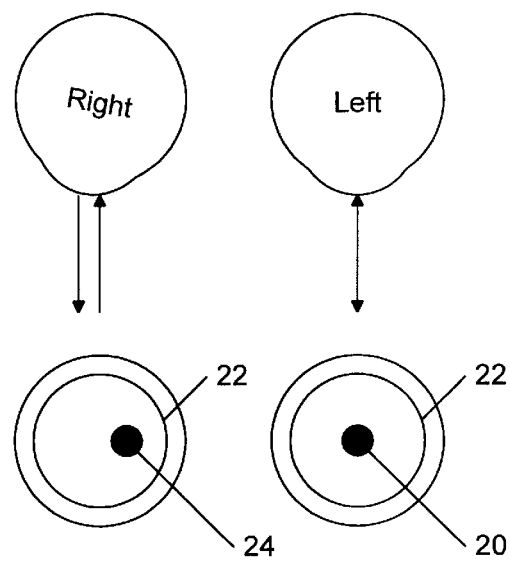
FIG. 2a                FIG. 2b
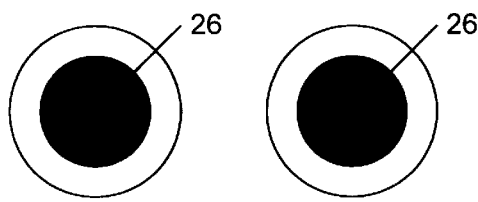
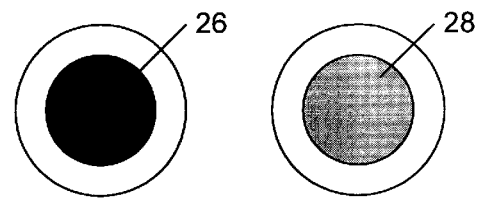
FIG. 2c                FIG. 2d
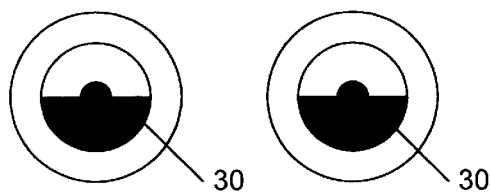
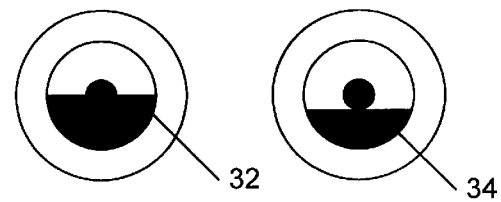
FIG. 2e                FIG. 2f

AUTOMATED PHOTOREFRACTIVE SCREENING

CLAIM OF PRIORITY

This application claims priority under 35 USC §119(e) to U.S. patent application Ser. No. 60/062,072, filed Oct. 15, 1997.

TECHNICAL FIELD

This invention relates to instruments for measuring characteristics of eyes, and more particularly to a system and method for locating and modeling eyes in imagery for automated photorefractive screening, and for enabling determination of the presence of anomalies in the patient's visual anatomy.

BACKGROUND

A well-known eye examination consists of shining a light into the interior of the eye and visually inspecting the uniformity of the reflected light, normally visible as a red color filling the pupil. Any deviation from uniformity, either in one eye or between the pair of eyes, indicates a potential problem in the patient's visual anatomy. Such light refractive screening is thus a useful tool in patient eye care.

Ocular disorders such as strabismus, various forms of refractive errors (myopia, hyperopia, and astigmatism) and opacities of the ocular media are the leading causes of amblyopia, or vision loss. These combine to cause amblyopia in approximately 5% of the population. However, some form of visual problem, not necessarily leading to amblyopia, may be present in over 20% of children.

Amblyopia does not simply decrease visual acuity. In addition to loss of recognition acuity, there is loss of grating acuity, vernier acuity, sensitivity to contrast, distortions of shape, locations in space, motion and worsening of crowding stimulus. Moreover, amblyopia is the leading cause of monocular vision loss in people under the age of 30.

Although monocular vision loss does not impact intellectual capacity, strabismus and other disfiguring disorders can have a tremendous emotional impact. Undetected need for glasses obviously can make school performance more difficult during crucial early grades. Lack of early school success can compound itself and lead to unfulfilled scholastic potential. Further, there are professions in which outstanding visual performance is required. Delaying recognition of various visual disorders may limit children from these future career choices.

Human visual development can be considered as having three stages: (1) the period of development of visual acuity to approximately 3–5 years of age; (2) the period from which deprivation is effective in causing amblyopia, from a few months to 7–8 years; and (3) the period from which recovery from amblyopia can be attained partially or fully (time of amblyopia to at least teenage years).

Because of the foregoing, clinical intervention in amblyopia is most efficacious if it takes place as soon as possible. Over the last 20 years, investigators have shown that many strabismic and amblyopic states result in abnormal visual experience in early life and these can be prevented or reversed with early detection and intervention. Therefore, identification of the defect at the earliest possible moment is crucial. Some studies have suggested that, for the best possible outcome, this must occur within two years of birth.

Despite this, previous reports have shown the primary care physicians are not always utilizing currently available screening techniques. In fact, one large study estimated that pediatricians are screening less than 40% of children age three or younger. This may be because of impracticality, either from a clinical or practical standpoint.

In fact, the National Institute of Health has made it one of its priorities to improve detection of refractive errors, strabismus, and amblyopia in infants and young children. This priority calls specifically for the study of better, and more cost-effective public health methods for testing visual function in preverbal children. Thus, the inventors have perceived a need for automated photorefractive screening.

In order to perform automated photorefractive screening, accurate models of the eye are necessary. The inventors have determined that it would be useful to have an automated way of generating such models and presenting such models for diagnosis, either automatically or by a physician or other care-giver. Accordingly, the present invention is directed to a system and method for locating and modeling eyes in imagery for automated photorefractive screening, and for enabling determination of the presence of anomalies in the patient's visual anatomy.

The problem solved by the invention differs from other eye and face detection problems. Pupil-tracking may be accomplished via a head-mounted apparatus (for instance, see H. Kawai and S. Tamura, "Eye movement analysis system using fundus images", in *Pattern Recognition*, 19(1), 1986, pp. 77–84), which fixes the location of the eyes relative to an image. Eye tracking may be accomplished via a constrained updating of an eye model (for instance, see X. Xie, R. Sudhakar and H. Zhuang, "On improving eye feature extraction using deformable templates", in *Pattern Recognition Letters*, 27(6), 1994, pp. 791–799; A. Yuille and P. Hallinan, "Deformable Templates", Chapter 2 in *Active Vision*, MIT Press, 1992, pp. 21–38). Face recognition (for instance, see *International Conference on Automatic Face and Gesture Recognition*, proceedings of, edited by M. Bichsel; 1995; *Second International Conference on Automatic Face and Gesture Recognition*, proceedings of, 1996, in Killington, Vt.) may be accomplished using a variety of image transformations or feature extractions. Additional information may be found in several general image processing references, including K. Castleman, *Digital Image Processing*, Prentice-Hall, 1996; R. Haralick, L. Shapiro, *Computer and Robot Vision*, 1, 2, Addison, 1992; and R. Jain, R. Kasturi and B. Schunck, *Machine Vision*, McGraw-Hill, 1995.

SUMMARY

A system and method for locating and modeling eyes in imagery for automated photorefractive screening. The preferred embodiment of the invention includes a digital camera having a lens-mounted flash for obtaining a digital image of the face of an individual, and a suitably programmed processor, such as a general purpose digital computer, for locating an eye of the individual in the digital image, modeling structures in the eye, analyzing the digitized eyes of the individual for eye disease, and providing a recommendation for treatment.

More particularly, in one aspect, the invention includes a system and method for locating a patient's eyes in a digital image that includes each eye as illuminated by a near-axis flash, including automatically finding light reflexes in the digital images as indicative of the location of each eye. Automatically finding light reflexes includes analyzing such light reflexes to determine possible pupil and sclera borders. The invention further includes automatically fitting a corresponding model to such possible pupil and sclera borders, analyzing the model of each eye to determine possible abnormalities in each eye; and outputting a possible diagnosis for each eye based on such analyzing.

In another aspect, the invention includes a system and method for locating and modeling a patient's eyes in a digital image that includes each eye as illuminated by a near-axis flash, including finding and indicating bright spots in the digital images as possible corneal reflexes of each eye; finding and indicating red-black and black-white gradients, each comprising a set of gradient points, around such bright spots as possible pupil and sclera borders, respectively, of each eye; fitting a plurality of circles to subsets of such gradient points as possible models for each eye, each eye model having an associated strength; and sorting the eye models for each eye by strengths, and indicating the strongest corresponding eye model as best representing each eye. Another aspect of the invention includes measuring red reflexes and corneal reflexes from the indicated eye models as an indicator of anomalies in the patient's eyes. Yet another aspect of the invention includes generating a digital image of each of a patient's eyes with a camera having a flash positioned near to a center axis of a lens of the camera so as to generate images with bright, sharp light reflexes.

The target audience for the invention is previously unreached large populations, such as school children. In order to keep the imaging process simple and cheap, no special apparatus is used. By using the characteristics of a near-axis flash and novel processing techniques, the eyes may appear anywhere in the image of the patient's face (simplifying use of the invention by field eyecare practitioners), the eyes of the patient need not fill the camera image frame, the camera may be positioned at a distance from the patient that is not intrusive to the patient, and the patient's head need not be tightly constrained.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 2a is a diagram showing the light path from a flash to a pair of normal eyes and back to a camera, as well as the appearance of the corneal reflexes from the camera view.

FIG. 2b is a diagram showing the light path from a flash to a pair of eyes, one of which is abnormal, and back to a camera, as well as the appearance of the corneal reflexes from the camera view.

FIG. 2c is a diagram of the retinal reflex 26 for a pair of normal eyes, showing uniform reflectance equal in both eyes and no refractive error.

FIG. 2d is a diagram of the retinal reflex for a pair of eyes, one of which has a retinal pathology that causes lesser reflectance.

FIG. 2e is a diagram of the retinal reflex for a pair of eyes, each showing a crescent-shaped reflectance, which indicates the same type of refractive error in both eyes.

FIG. 2f is a diagram of the retinal reflex for two eyes, showing different crescent reflectances, which indicates differing amounts of refractive error in the eyes.

FIG. 6b is a close-up photograph of a patient's eye, showing black-to-white gradient points located for the image in FIG. 6a.

Like reference numbers and designations in the various drawings indicate like elements.

DETAILED DESCRIPTION

Imaging System

Figure 1A:
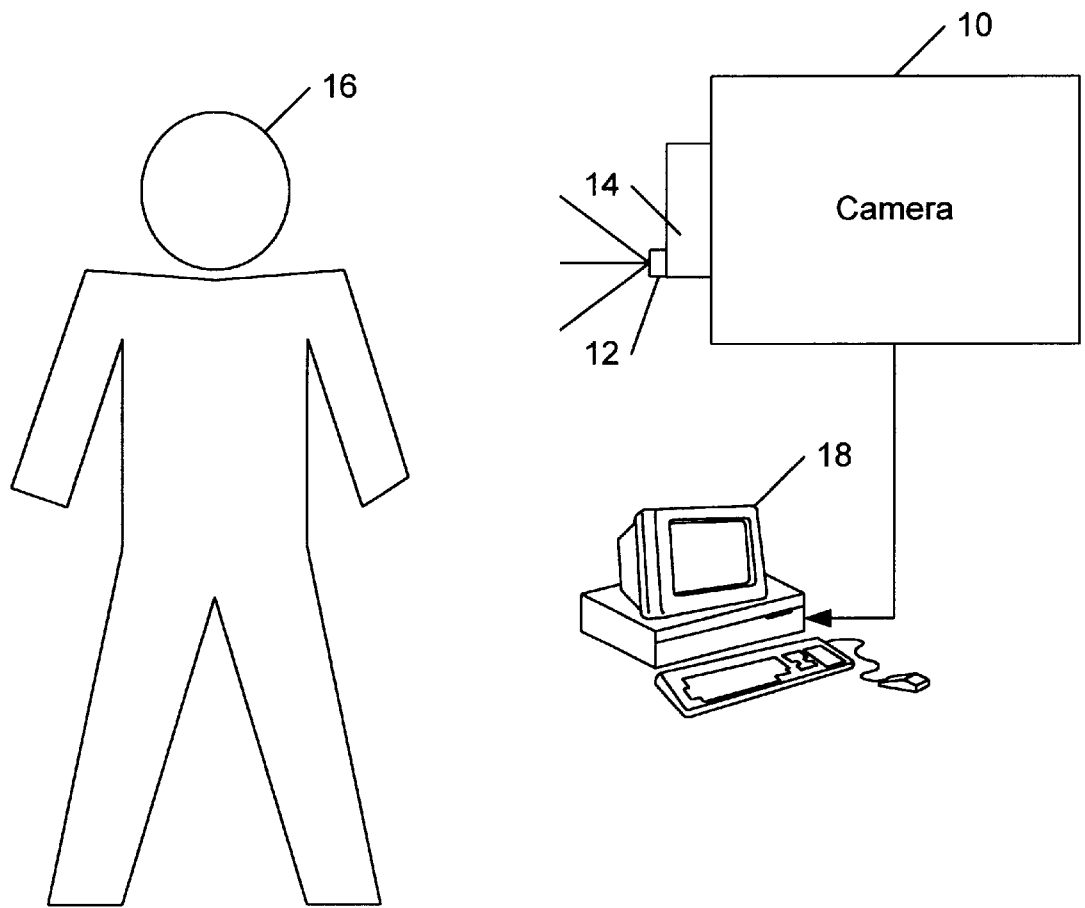
FIG. 1a is block diagram showing the preferred physical components of the invention as used for imaging an eye of a patient.

FIG. 1a is block diagram showing the preferred physical components of the invention as used for imaging the eyes of a patient. A digital camera 10 is modified to include a "near-axis" flash 12 positioned slightly off the optical axis of the lens 14 of the camera 10. The flash 12 may be, for example, a ring flash or one or more small flash units attached near the optical axis of the lens 14 of the camera 10. A suitable camera is the Model DC120 Digital Camera from Kodak Corporation, with an attached 6X telephoto lens 14 and a small flash unit 12 mounted to the front of the telephoto lens, slightly off-center. The telephoto lens increases the field of view of the camera as it images the patient's eye, thus increasing the number of pixels available for analysis.

Figure 1B:
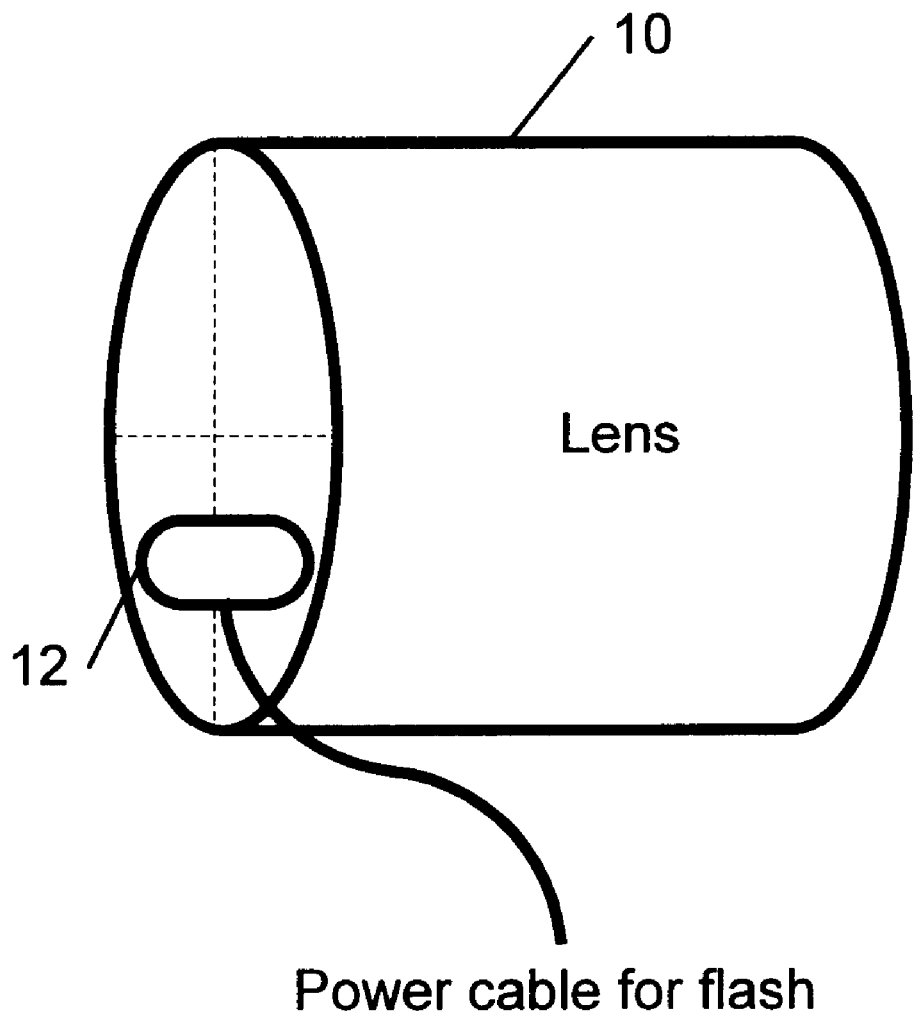
FIG. 1b is a perspective view of a lens 14 and flash 12 in accordance with the invention.

The proximity of the flash 12 to the center of the lens 14 provides bright, sharp light reflections (reflexes) that enable the image processing aspects of the invention to model the patient's eyes accurately and reliably. Use of a flash rather than continuous lighting means that the patient's pupils can be fully open without causing significant discomfort to the patient. FIG. 1b is a perspective view of a lens 14 and flash 12 in accordance with the invention. The flash 12 in the illustrated embodiment uses visible light. However, a flash that principally emits non-visible light, such as infrared flash, may be used instead with a suitable camera 10.

The camera 10 is used to capture and directly download a digital image of the face of a patient 16 to a conventional computer 18 for processing. In the preferred embodiment of the invention, the camera 10 is used to obtain a high quality digital image of the patient's face and eyes, preferably a full-color (e.g., RGB), high resolution (e.g., 8 bits per pixel for each color) image of about at least 640×480 pixels in size, and preferably about at least 1024×768 pixels in size. Although a color image is preferred, the techniques of the invention can be applied to gray-scale images. However, for purposes of this explanation, a color digital image will be assumed.

In an alternative embodiment, the camera 10 may be a conventional film camera, such as an instant photography camera, the images of which are optically scanned into the computer 18. In another alternative embodiment, processing of the image in accordance with the invention is done within a specially programmed digital camera 10, allowing for an integrated photoscreening system.

Photoscreening

Photoscreening works by photographing two distinct light reflexes from the eye, a corneal reflex and a retinal reflex. Light from a flash 12 is bounced off of the air-tear film interface on the cornea of the eye. Since the corneal surface is essentially spherical, the closest point of the cornea to the camera 10 will reflect the light flash back to the camera as a corneal reflex. If the eye faces the camera, the light reflection point is normally centered in the pupil of the eye. If the eye has strabismus or a related defect, the light reflection point is not centered on the pupil.

Several corneal reflex conditions are shown in FIGS. 2a–2a is a diagram showing the light path from a flash to a pair of normal eyes and back to a camera, as well as the appearance of the corneal reflexes from the camera view. As shown, the corneal light reflex 20 is essentially centered within the outline of the iris 22. FIG. 2b is a diagram showing the light path from a flash to two eyes, one of which is abnormal, and back to a camera, as well as the appearance of the corneal reflexes from the camera view. As shown, the corneal light reflex 20 is essentially centered within the outline of the iris 22 for the left eye, but the corneal light reflex 24 for the right eye is off-center. Note that the tolerance of "centered" depends in part on the displacement of the flash 12 from the optical axis of the camera lens 14.

Light from a flash 12 also bounces off of the back of the eye through the retina. The retinal light reflex gives information on ocular pathologies and the refractive state of the eye. If one eye has any pathology (e.g., a tumor, blood, cataract, etc.), the retina does not reflect as much light as in a normal eye. The difference in reflectance between an abnormal retina and a normal retina is noticeable. Also, in an eye without refractive error, the retinal light reflex appears as a uniformly bright circle. If the eye has any refractive error, a crescent will appear in the retinal light reflex. The relative size of the crescent to the pupil diameter is generally related to the refractive error. Thus, the differences in reflectance that may be perceived can be global (differences between eyes) or local (differences in areas of an eye).

Several retinal reflex conditions are shown in FIGS. 2c–2f. FIG. 2c is a diagram of the retinal reflex 26 for a pair of normal eyes, showing uniform reflectance equal in both eyes and no refractive error. FIG. 2d is a diagram of the retinal reflex for a pair of eyes, one of which has a retinal pathology that causes lesser reflectance 28. FIG. 2e is a diagram of the retinal reflex for a pair of eyes, each showing a crescent-shaped reflectance 30, which indicates the same type of refractive error in both eyes. FIG. 2f is a diagram of the retinal reflex for a pair of eyes, showing different crescent reflectances 32, 34, which indicates differing amounts of refractive error in the eyes.

Eye Model

In order to automate photoscreening, a model of the eyes in an image of a patient's face must be generated. In the preferred embodiment of the invention, the frontal projection of an eye is modeled by a pair of concentric circles:

$$(x-A)^2+(y-B)^2=C_1^2 \quad (1)$$

$$(x-A)^2+(y-B)^2=C_2^2 \quad (2)$$

where (A, B) are the coordinates for the center of the eye, $C_1$ denotes the boundary between the pupil and iris, and $C_2$ denotes the boundary between the iris and sclera. This model locates the eye in a two-dimensional coordinate system and establishes a means to measure the reflexes from the eye. After model parameters are generated, the model may be used to automatically generate a diagnosis or screening decision for the eye anatomy.

Figure 3A:
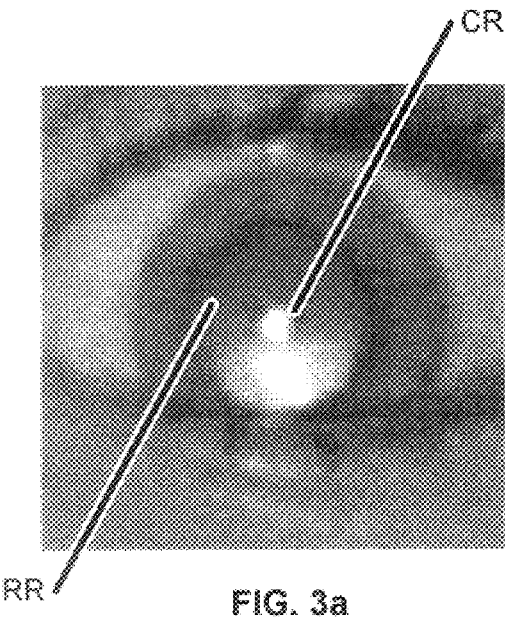
FIG. 3a is a close-up photograph of a patient's eye.
Figure 3B:
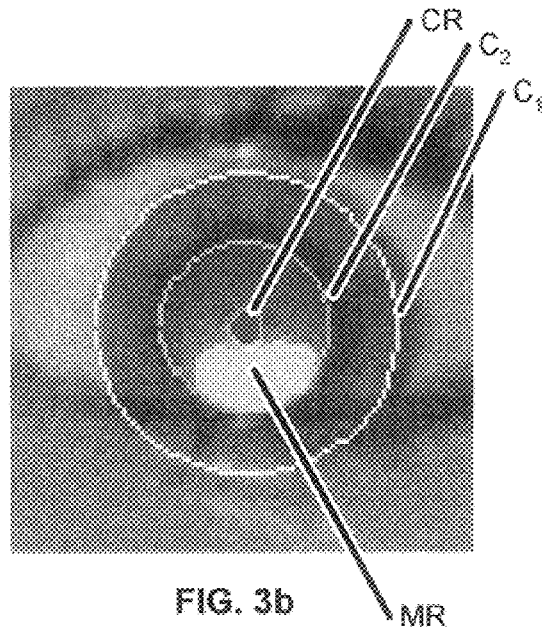
FIG. 3b is a close-up photograph of a patient's eye with a superimposed graphical representation of the eye model used in the invention.
Figure 4A:
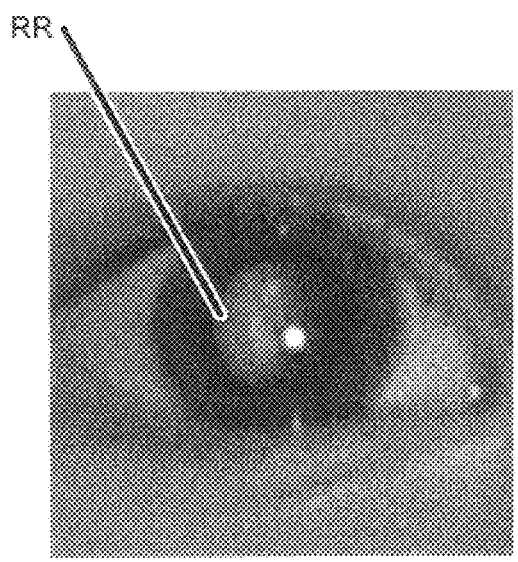
FIG. 4a is a close-up photograph of a patient's eye containing an abnormal pupil area
Figure 4B:
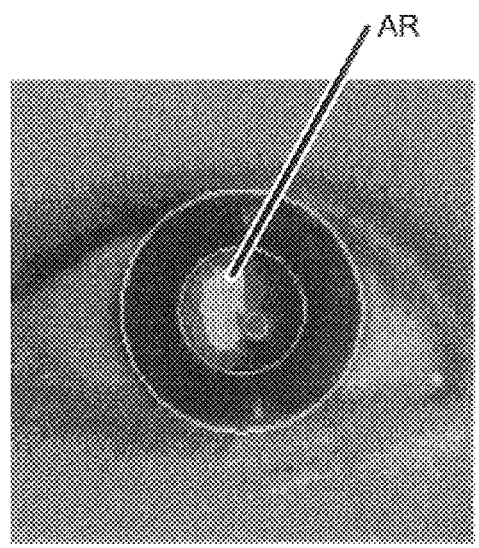
FIG. 4b is a close-up photograph of a patient's eye containing an abnormal pupil area with a superimposed graphical representation of the eye model used in the invention.

As an example of how such a model "fits" an eye, FIG. 3a is a close-up photograph of a patient's eye, while FIG. 3b is a close-up photograph of a patient's eye with a superimposed graphical representation of the eye model used in the invention. $C_1$ denotes the iris-pupil boundary, and $C_2$ denotes the iris-sclera border. As another example, FIG. 4a is a close-up photograph of a patient's eye containing an abnormal pupil area FIG. 4b is a close-up photograph of a patient's eye containing an abnormal pupil area with a superimposed graphical representation of the eye model used in the invention.

In the preferred embodiment of the invention, a set of reflexes is measured for each eye. The corneal reflex is the reflection of light from the front surface of the eye (the cornea). It typically appears as a bright spot. The corneal reflex CR is modeled as a four-connected region (defined below). In FIG. 3b, the corneal reflex is indicated by an overlayed region CR. (Note that the corneal reflex CR in FIG. 3b is not necessarily located at the center of the model.) The corneal reflex is always present in an image of the eyes taken through the camera 10 and flash 12 described above. This fact is used to automatically locate the eyes in an image of a patient's face, even if the eyes do not fill the camera image frame.

The retinal (or red) reflex RR is part of the pupillary reflex, the reflection of light from the inner surface (retina) of the eye, returning back through the pupil. In a color image, the retinal reflex typically fills the pupil with a reddish tint. In the preferred embodiment, the retinal reflex RR is modeled as a single intensity value corresponding to the average amount of red color visible in the pupil. (In a grayscale image, the retinal reflex should appear as a distinctly identifiable set of gray values, and could be similarly modeled).

The crescent reflex MR is also part of the pupillary reflex. Depending on the curvature of the eye, and the location of the flash, a stronger concentration of reflected light, usually crescent-shaped, may appear around a portion of the boundary of the pupil. When present, the crescent reflex MR is preferably modeled as a four-connected region (defined below). In FIG. 3b, the crescent reflex has been displayed by an overlayed region MR.

Other anatomical problems can also cause a non-uniform pupillary reflex. For instance, a cataract can cause a portion of the pupillary reflex to appear brighter than normal. These "other" abnormal pupil areas may occur in any portion of the pupillary reflex. When present, each abnormal pupil area AR is modeled as a four-connected region (defined below). In FIG. 4b, an abnormal pupil area has been displayed by an overlayed region AR.

A four-connected region is defined as follows. Formally, let I denote an image, consisting of a two-dimensional raster of pixels, organized on an integer grid of R rows and C columns. Let (r, c) denote a pixel location in image I. A four-connected path P between two pixels $(r_i, c_i)$ and $(r_j, c_j)$ is defined as:

$$P((r_i, c_i), (r_j, c_j)) = \{(r_1, c_1), (r_2, c_2), (r_3, c_3), \ldots, (r_N, c_N)\}, \quad (3)$$

where $$(r_{x+1}, c_{x+1}) = \begin{cases} (r_x + 1, c_x) \text{ or} \\ (r_x - 1, c_x) \text{ or} \\ (r_x, c_x + 1) \text{ or} \\ (r_x, c_x - 1) \end{cases} \forall x = 1 \ldots N-1,$$

$$0 \leq r_x < R, 0 \leq c_x < C,$$

$$(r_i, c_i) = (r_1, c_1) \text{ and } (r_j, c_j) = (r_N, c_N)$$

A four-connected region S is defined as:

$$S = \{(r_1, c_1), (r_2, c_2), (r_3, c_3), \ldots, (r_N, c_N)\}, \text{ where}$$

$$P((r_i, c_i), (r_j, c_j)) \text{ exists } \forall i, j \in N \quad (4)$$

Informally, Eq. 4 describes any set of pixels in I contiguously connected, such that any pixel in the set may be reached from any other pixel in the set by at least one path of pixels also in the set. In the preferred embodiment, the possible as well as actual corneal reflexes, crescent reflexes, and other abnormal pupil areas, as described in this work, are all modeled as four-connected regions.

Locating, Modeling, Analyzing, and Diagnosing Eyes

One aspect of the invention is to derive necessary parameters from a digitized image of a patient's face and eyes sufficient to locate each eye and generate a model for each eye as described above. To accomplish this goal, the invention advantageously utilizes the characteristics of a particular illuminating flash, which produces light reflexes not seen in normal intensity imagery. The preferred embodiment of the invention specifically takes advantage of such light reflexes using special image processing to locate and model the eye so as to enable automated photorefractive screening.

More particularly, the presumed content of the camera image generated as described above is used advantageously to reduce the complexity of the search for possible eye models. Each eye is assumed to contain a corneal reflex CR, which appears as a saturated (bright) spot somewhere inside the pupil. Each pupil is assumed to contain some amount of red shading, which creates a prominent gradient in the red band at the pupil-iris boundary. (This is referred to below as the "red-black" gradient for convenience. However, a similar boundary can be ascertained in gray scale images as distinct differences in grayscale gradients.) Each sclera is assumed to appear as a shade of white, which creates a prominent gradient in full color at the iris-sclera boundary. (This is referred to below as the "black-white" gradient for convenience. A similar boundary can be ascertained in gray scale images as distinct differences in grayscale gradients.) These three features drive the search process.

Figure 5:
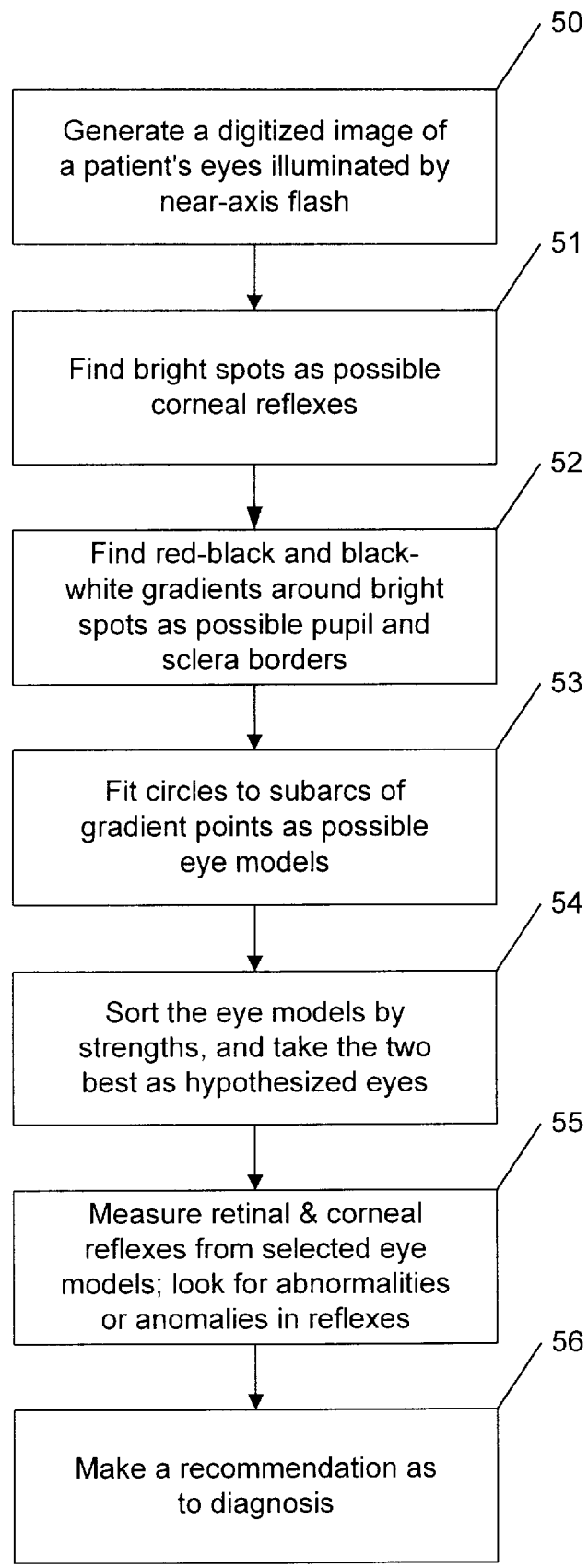
FIG. 5 is a flowchart showing an overview of the steps of the image processing of the preferred embodiment of the invention.

FIG. 5 is a flowchart showing an overview of the steps of the image processing of the preferred embodiment of the invention. In broad terms, the steps of the preferred process for locating, modeling, analyzing, and diagnosing a patient's eyes are as follows, each of which is discussed more fully below:

(1) Generate a digitized image of a patient's face and eyes, as illuminated by a near-axis flash (STEP 50).

(2) Find bright spots in the image as possible corneal reflexes (STEP 51).

(3) Find red-black and black-white gradients around bright spots as possible pupil and sclera borders (STEP 52).

(4) Fit circles to subarcs of gradient points as possible eye models (STEP 53).

(5) Sort the eye models by strengths (i.e., the likelihood of being correct models of an eye), and take the two best as hypothesized eyes (STEP 54) (this assumes that the patient has two eyes).

(6) Measure retinal and corneal reflexes from the selected eye models, and look for abnormalities or anomalies in such reflexes (STEP 55).

(7) Make a recommendation as to diagnosis (STEP 56).

(1) Generate a digitized image of a patient's face and eyes, as illuminated by a near-axis flash As noted above, the camera 10 and near-axis flash 12 are used to capture an image of a patient's face and eyes. If the camera 10 is digital, the image data may be directly downloaded to the computer 18 for processing as a digital image. If the camera 10 is a conventional film camera, such as an instant photography camera, the images are optically scanned into the computer 18 and stored as a digital image. The unprocessed images may be displayed on a computer monitor or printed (monochrome or color), and may be annotated using suitable conventional graphics software.

(2) Find bright spots in the image as possible corneal reflexes

Each three-band (i.e., RGB) image input into the computer 18 is preferably thresholded in each band to locate areas that are possible corneal reflexes. The images are logically AND'd together to produce a binary image of bright areas. Bright pixels are then spatially grouped into four-connected regions using a queue-based paint-fill algorithm. Bright regions with areas within a selected size range are labeled as possible or hypothesized corneal reflexes.

Formally, the input image I is thresholded to produce a binary image $I_{bright}$ indicating which pixels are bright:

$$I_{bright} = \begin{cases} 1 & I_{red} \geq T_B, I_{green} \geq T_B, I_{blue} \geq T_B \\ 0 & \text{otherwise} \end{cases} \quad (5)$$

where $I_{red}$, $I_{green}$ and $I_{blue}$ are the individual band values of the input image, $I_{bright}=1$ indicates a pixel is bright, and $T_B$ is a selected threshold value. A queue-based paint-fill algorithm is then applied to spatially group bright pixels into four-connected regions using. The pseudocode for this algorithm is given below (the image I referred to in the pseudocode in this case is the bright image $I_{bright}$):

initialize LABEL=2 for each pixel P in the image I
  if I(P)=1
    let Q be an empty queue of pixel indices add P to Q
      increase LABEL by 1 set I(P)=LABEL until Q is empty do:
        select the top point, X, from Q for all 4-connected neighbors N of X do:

```
if I(N) = 1
    add N to Q
    set I(P) = LABEL
end if
end for
```

-continued

```
            remove X from Q
         end until
      end if
   end for
```

Thereafter, the size of each bright region is counted as the number of pixels with the same label:

$$\text{size}_{LABEL} = \sum_{r,c} \begin{cases} 1 & I_{bright} = \text{LABEL} \\ 0 & \text{otherwise} \end{cases} \quad (6)$$

where (r, c) denotes all pixel locations in the image. Regions satisfying $$T_S \leq \text{size}_{LABEL} \leq T_L \quad (7)$$

are considered to be possible corneal reflexes, where $T_S$ and $T_L$ are selectable threshold values.

(3) Find red-black and black-white gradients around bright spots as possible pupil and sclera borders For each possible corneal reflex (region) LABEL, a set of pixels is found circularly around the corneal reflex, at distances within the expected range of pupil and iris radii, that exhibit strong gradients. This is accomplished by considering the centroid of the region, together with pixels along an evenly distributed set of compass directions from the centroid, as forming a set of rays. A linear gradient filter is applied to the pixels along a segment of each ray. For each segment, the pixel with the highest black-to-white gradient and the pixel with the highest red-to-black gradient are noted. Any direction for which the highest gradient points are not within the expected ranges of distance from the centroid, or for which the black-to-white gradient is closer to the centroid than the red-to-black gradient, are discarded as outlying stray pixels ("outliers").

Formally, the centroid $(x_c, y_c)$ of the four-connected region with the value LABEL is found as:

$$x_c = \left[ \frac{\sum_{r,c} \begin{cases} c & I_{bright} = \text{LABEL} \\ 0 & \text{otherwise} \end{cases}}{\text{size}_{LABEL}} \right] \quad (8)$$

$$y_c = \left[ \frac{\sum_{r,c} \begin{cases} r & I_{bright} = \text{LABEL} \\ 0 & \text{otherwise} \end{cases}}{\text{size}_{LABEL}} \right]$$

The centroid, together with an equiangular set of compass directions, forms a set of rays:

$$(x_c, y_c) \ldots (x_c + \cos\theta, y_c + \sin\theta) \; \theta = 0, T_\theta, 2T_\theta, 3T_\theta, \ldots 360 \quad (9)$$

where $T_\theta$ (degrees) is a selectable algorithm parameter that controls the angular resolution of the set. The pixels (integer coordinates) along each ray $\theta$ are enumerated between:

$$(x_c + T_1 \cos\theta, y_c + T_1 \sin\theta) \ldots (x_c + T_4 \cos\theta, y_c + T_4 \sin\theta) \quad (10)$$

according to the pseudocode set forth below, and T, and $T_4$ are algorithm parameters describing the minimum and maximum expected radius (in pixels) of the pupil and iris, respectively.

```
given x1, y1, x2, y2 (integers) if x1>x2 then sway x1, y1
   with x2, y2 let x,y (real-valued variables)=x1, y1 loop
      add floor(x,y) to list if x2-x1>|y2-y1|then
         x=x+1 y=y+(y2-y1)/(x2-x1)
      else
         if y2>y1 then y=y+1 else y=y-1 x=x+(x2-x1)/(|y2-
            y1|)
      end if
   until |x2-x|>0.5 and |y2-y|<0.5 if swapped at beginning,
      reverse list
```

After such enumeration, let the list of points along each ray $\theta$ be denoted as:

$$RAY_{\theta:i} = (x_{\theta:i}, y_{\theta:i}) \; i = 1 \ldots N_\theta$$

$$= \{(x_{\theta:1}, y_{\theta:1}), (x_{\theta:2}, y_{\theta:2}), \ldots, (x_{\theta:N\theta}, y_{\theta:N\theta})\} \quad (11)$$

where $N\theta$ is the number of points in the list returned by the above pseudocode.

TABLE 1

| -1 | -1 | -1 | 0 | 1 | 1 | 1 |
|----|----|----|---|---|---|---|

A 1×7 linear gradient filter, shown in Table 1 above, is convolved with the points along the ray to compute a black-to-white gradient $BW_{\theta:i}$ (Eq. 12) and a red-to-black gradient $RB_{\theta:i}$ (Eq. 13) estimate at each pixel on each ray:

$$BW_{\theta:i} = \sum_{j=1}^{3} (I_{red}(RAY_{\theta:i+j}) - I_{red}(RAY_{\theta:i-j}) + I_{green}(RAY_{\theta:i+j}) - \quad (12)$$

$$I_{green}(RAY_{\theta:i-j}) + I_{blue}(RAY_{\theta:i+j}) - I_{blue}(RAY_{\theta:i-j})),$$

$$i = T_3 \ldots N_\theta - c$$

$$RB_{\theta:i} = \sum_{j=1}^{3} (I_{red}(RAY_{\theta:i-j}) - I_{red}(RAY_{\theta:i+j})) \; i = 3 \ldots T_2 \quad (13)$$

where $T_2$ and $T_3$ are algorithm parameters describing the maximum and minimum expected radius (in pixels) of the pupil and iris, respectively.

The pixel with the strongest black-to-white gradient, $RAY_{\theta:w}$, is found such that:

$$BW_{\theta:w} \geq BW_{\theta:i} \; \forall i = 3 \ldots N_\theta - 3 \quad (14)$$

The pixel with the strongest red-to-black gradient, $RAY_{\theta:r}$, is found such that:

$$RB_{\theta:r} \geq RB_{\theta:i} \; \forall i = 3 \ldots N_\theta - 3 \quad (15)$$

These pixels form two lists of points, radially ordered about the possible corneal reflex, one point per ray for each list. The list of black-to-white gradient points is denoted as:

$$RAY_{\theta:w} = (x_{\theta:w}, y_{\theta:w}) \; \theta = 0, T_\theta, 2T_\theta, 3T_\theta, \ldots 360$$

$$= \{(x_{\theta:w}, y_{\theta:w}), (x_{T\theta:w}, y_{T\theta:w}), (x_{2T\theta:w}, y_{2T\theta:w}), \ldots (x_{360:w}, y_{360:w})\} \quad (16)$$

The list of red-to-black gradient points is denoted as:

$$RAY_{\theta:r} = (x_{\theta:r}, y_{\theta:r}) \; \theta = 0, T_\theta, 2T_\theta, 3T_\theta, \ldots, 360$$

$$= \{(x_{\theta:r}, y_{\theta:r}), (x_{T\theta:r}, y_{T\theta:r}), (x_{2T\theta:r}, y_{2T\theta:r}), \ldots, (x_{360:r}, y_{360:r})\} \quad (17)$$

Since these lists form closed loops, the point $RAY_{\theta:i} = RAY_{\theta-360:i} = RAY_{\theta+360:i}$ by cyclic wrap-around.

(4) Fit circles to subarcs of gradient points as possible eye models

Using a least-squares solution, circle equations are fit to the gradient points discovered in the previous step. For each possible corneal reflex, one circle is fit to the black-to-white gradient pixels and one circle is fit to the red-to-black gradient points. The preferred embodiment of the invention uses a novel method for eliminating outliers in the circle fit, based upon subarcs. The removal of outliers as arc subsets follows naturally from the problem context. If an eye is imaged in a non-forward orientation, or if an eyelid covers some portion of the iris, or if the retinal reflex fills only part of the pupil, then fitting a circle to the strongest large subarc generally yields the most reliable model.

More particularly, using a least-squares solution, a circle equation is fit to eight subsets of each type of gradient point. Each subset covers 270° of arc, starting at 45° increments. Three strength measures are computed for each circle fit: residual, average gradient, and arc coverage. These values are normalized and summed as a strength score. The circle (out of 8 possible, in the illustrated embodiment) with the overall best strength score is taken as the model for the given hypothesized corneal reflex.

Formally, let a set of pixels to be modeled by a circle:

$$(x-a)^2+(y-b)^2=r^2 \tag{18}$$

be denoted as:

$(x_i, y_i)\ i=1\ldots N$ $$=\{(x_1, y_1),(x_2, y_2),\ldots,(x_N, y_N)\} \tag{19}$$

where a, b and r are the model parameters and N is the number of points to be modeled. The following procedure is used to derive the pupil-iris boundary (model $(A,B,C_1)$, Eq. 1) from the set of red-to-black gradient points ($RAY_{\theta:r}$, Eq. 17) and the iris-sclera boundary (model $(A,B,C_2)$, Eq. 2) from the set of black-to-white gradient points ($RAY_{\theta:w}$, Eq. 16). In the first case, the substitution of notation is $(a,b,r)=(A,B,C_1)$ and $(x_{\theta:r}, y_i)=(x_{\theta:r}, y_{\theta:r})$, where i increments by one as $\theta$ increments by $T_\theta$, and $N=360/T_\theta$. In the second case, the substitution of notation is $(a,b,r)=(A,B,C_2)$ and $(x_i,y_i)=(x_{\theta:w}, y_{\theta:w})$, where i increments by one as $\theta$ increments by $T_\theta$, and $N=360/T_\theta$.

Let $\chi$ denote an error term which sums the distances between the model (a,b,r) and each point $(x_i, y_i)$ to give the least-squares fitting problem:

$$\chi^2(a, b, r) = \sum_{i=1}^{N} (r^2 - (x_i - a)^2 - (y_i - b)^2)^2 \tag{20}$$

where the solution is the model that minimizes $\chi^2$.
Expanding Eq. 20 yields:

$$\chi^2(a, b, r) = \sum_{i=1}^{N} (r^2 - x_i^2 + 2x_i a - a^2 - y_i^2 + 2y_i b - b^2)^2 \tag{21}$$

Using the substitution:

$$\alpha=a^2+b^2-r^2 \tag{22}$$

in Eq. 21 yields:

$$\chi^2(a, b, \alpha) = \sum_{i=1}^{N} (-x_i^2 + 2x_i a - y_i^2 + 2y_i b - \alpha)^2 \tag{23}$$

which may be recognized as linear in the unknowns a, b and $\alpha$. Given these conditions, a solution to Eq. 23 may be found by use of the well-known normal equations (for instance, see W. Press et al., *Numerical Recipes in C: The Art of Scientific Computing*, Cambridge Press, (2nd edition) 1992), written in matrix form as:

$$Ax=b \tag{24}$$

where A is N×3, x is 3×1, b is N×1, and the matrices are constructed as:

$$\begin{bmatrix} 2x_1 & 2y_1 & -1 \\ 2x_2 & 2y_2 & -1 \\ \cdots \\ 2x_N & 2y_N & -1 \end{bmatrix} \begin{bmatrix} a \\ b \\ \alpha \end{bmatrix} = \begin{bmatrix} x_1^2 & y_1^2 \\ x_2^2 & y_y^2 \\ \cdots \\ x_N^2 & y_N^2 \end{bmatrix} \tag{25}$$

The solution to Eq. 24 is:

$$x=(A^T A)^{-1} A^T \tag{26}$$

from which a and b are found directly, and r is found by substitution back into Eq. 22. In the preferred embodiment, the Gauss-Jordan elimination method (see, for example, W. Press et al., *Numerical Recipes in C: The Art of Scientific Computing*, Cambridge Press, (2nd edition) 1992) is used to solve the matrix inversion in Eq. 26.

Figure 6A:
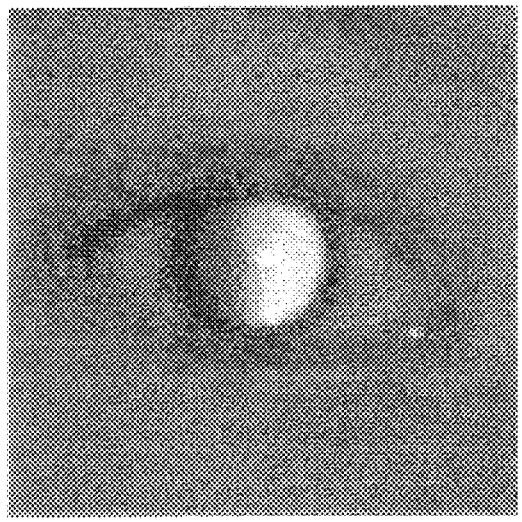
FIG. 6a is a close-up photograph of a patient's eye without a superimposed model.
Figure 6B:
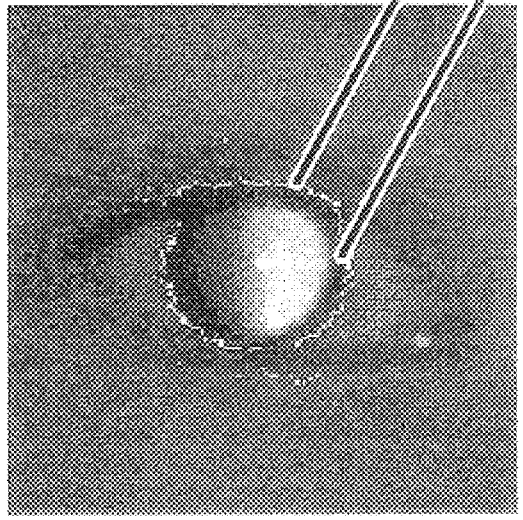

Eq. 26 yields the optimal solution (best model) if all points $(x_i,y_i)$ are "inliers", and the measurement noise is uniformly distributed. The points located via strong gradients rarely meet these constraints. For instance, FIGS. 6a–6d are close-up photographs of a patient's eye, showing various stages in the removal of outliers. FIG. 6a is a close-up photograph of a patient's eye without a superimposed model. FIG. 6b shows the black-to-white gradient points 60 located for the image in FIG. 6a. These pixels illustrate a spurious response to an eyelid as well as some unstructured outliers.

A popular method for fitting in the presence of outliers is the least-median-of-squares method (see, e.g., P. J. Rousseeuw, "Least median of squares regression", in *Journal of American Statistics Association*, vol. 79, 1984, pp. 871–880, and P. Meer, D. Mintz and A. Rosenfeld, "Robust Regression Methods for Computer Vision: A Review", in *International Journal of Computer Vision*, 6:1, 1991, pp. 59–70). This algorithm works in the presence of up to 50% outliers, but is $O(n^2)$ in computational complexity.

To avoid slow computation, the preferred embodiment uses several constraints combined with a novel method to eliminate outliers in O(n) time:

(a) Any pixel RAY:,w is discarded for which:

$$RB_{\theta:w} \leq 100 \tag{27}$$

(b) Any pixel RAYO:r is discarded for which:

$$BW_{\theta:r} \leq 100 \tag{28}$$

In both cases (a) and (b), a gradient below 100 implies an almost imperceptible boundary that is probably a response to noise.

(c) Any pixel that is a duplicate of another pixel is discarded:

$$(x_i, y_i)=(x_j, y_j), i \neq j \tag{29}$$

Such duplicate pixels may appear if $T_\theta$ is too small, resulting in oversampling.

(d) For any pixel-pair $RAY_6:w$ and $RAY_{\theta:r}$, the pixel $RAY_{\theta:r}$ is discarded if:

$$w \leq r - 3 \qquad (30)$$

This applies the natural constraint that the iris boundary must be outside the pupil boundary.

(e) If a pixel is found to be isolated, it is discarded. A pixel $(x_i, y_i)$ is considered not to be isolated if:

$$\sqrt{(x_{j+1} - x_j)^2 + (y_{j+1} - y_j)^2} \leq 2.5 \quad j = i-4 \ldots i+3 \qquad (31)$$

Figure 6C:
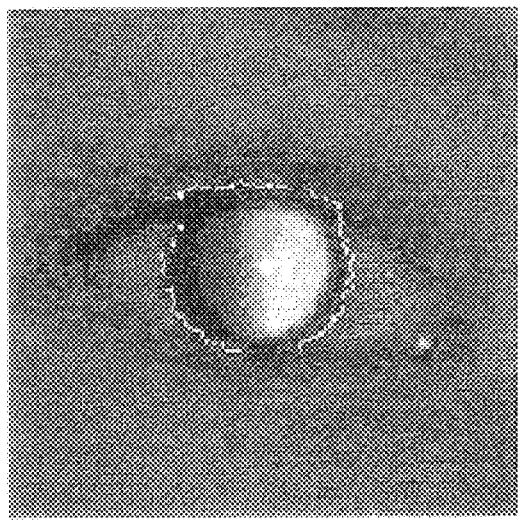
FIG. 6c is a close-up photograph of a patient's eye, illustrating the result of applying constraints to the black-to-white gradient points shown in FIG. 6b.

All discarded pixels are treated as outliers in that they are not used during the least-squares fitting procedure. FIG. 6c illustrates the result of applying Eq. 27–31 to the black-to-white gradient points shown in FIG. 6b. Note that only the unstructured outliers have been removed from the image. A set of structured outliers (due to a response from the eyelid) are still present.

For the remaining inliers, Eq. 26 is applied to eight subsets of the points $RAY_{\theta:w}$ and to eight subsets of the points $RAY_{\theta:r}$. Each subset is formed by a set of points within a prescribed range of $\theta$. The effect is that each subset contains points on a subarc of the original sampling circle. Formally, eight subsets of $RAY_{\theta:w}$ and of $RAY_{\theta:r}$ are respectively defined as:

$$SUBARC_{\delta:\theta:w} = (x_{\delta+\theta:w}, y_{\delta+\theta:w}) \; \theta=0, T_\theta, 2T_\theta, \ldots, 270 \; \delta=0, 45, \ldots, 315 \qquad (32)$$

$$SUBARC_{\delta:\theta:r} = (x_{\delta+\theta:r}, y_{\delta+\theta:r}) \; \theta=0, T_\theta, 2T_\theta, \ldots, 270 \; \delta=0, 45, \ldots, 315 \qquad (33)$$

Each subset describes the gradient points located in 270° of contiguous arc around the possible corneal reflex, starting at 45° increments.

For each subset $SUBARC_{\delta:\theta:w}$ or $SUBARC_{\delta:\theta:r}$ and its resulting (a,b,r), the residual, average gradient strength, and arc coverage are used to calculate a score. The score values all depend upon the number of inliers used for fitting the circle. This number, denoted $N_{in}$, is computed as $360/T_\theta$ (the number of pixels in the original set $RAY_{\theta:w}$ or $RAY_{\theta:r}$) minus the count of pixels discarded or omitted by any of the appropriate steps given in Eq. 27–33.

The residual is computed as:

$$\text{residual} = \frac{1}{N_{in}} \sum_{i=1}^{N} \begin{cases} \left| r - \sqrt{(x_i - a)^2 + (y_i - b)^2} \right| & (x_i, y_i) \in \text{inliers} \\ 0 & \text{otherwise} \end{cases} \qquad (34)$$

The average gradient strength for each $SUBARC_{\delta:\theta:w}$ is computed as:

$$\text{gradient}_{BW} = \frac{1}{N_{in}} \sum_{i=1}^{N} \begin{cases} BW_{i:w} & (x_i, y_i) \in \text{inliers} \\ 0 & \text{otherwise} \end{cases} \qquad (35)$$

The average gradient strength for each $SUBARC_{\delta:\theta:r}$ is computed as:

$$\text{gradient}_{RB} = \frac{1}{N_{in}} \sum_{i=1}^{N} \begin{cases} RB_{i:r} & (x_i, y_i) \in \text{inliers} \\ 0 & \text{otherwise} \end{cases} \qquad (36)$$

The arc coverage is computed as:

$$\text{coverage} = \frac{N_{in}}{2\pi r} \qquad (37)$$

where r is the radius of the fitted circle. If coverage <0.3, then the subset is deemed unreliable (the fitted points span only 30% or less of the circle boundary). If all eight subsets $SUBARC_{67\,:\theta:r}$ and all eight subsets $SUBARC_{\delta:\theta:w}$ are deemed unreliable, then the possible corneal reflex LABEL is disproved as a candidate eye model. The scores for $\text{gradient}_{BW}$ and $\text{gradient}_{RB}$ are capped at 500; any larger value is set to 500. The scores for each $SUBARC_{\delta:\theta:r}$ and $SUBARC_{\delta:\theta:w}$ are respectively computed as:

$$\text{score}_{\delta:r} = 1.0 - \frac{\text{residual}}{1.5} + \frac{\text{gradient}_{RB}}{500} + \text{coverage} \qquad (38)$$

$$\text{score}_{\delta:w} = 1.0 - \frac{\text{residual}}{1.5} + \frac{\text{gradient}_{RW}}{500} + \text{coverage} \qquad (39)$$

The maximum score in each case is 3. The weighting factors were derived experimentally.

If at least one subset of red-to-black gradient points $SUBARC_{67\,:\theta:r}$ is deemed reliable, then the highest scoring subset $SUBARC_{\Delta:\theta:r}$ is found such that:

$$\text{score}_{\delta:r} \geq \text{score}_{\delta:r} \; \forall \delta = 0, 45, \ldots 315 \qquad (40)$$

The parameters (a,b,r) of the circle fitted to the points $SUBARC_{\delta:\theta:r}$ are used to derive the parameters for a possible pupil-iris boundary (Eq. 1) as follows: A=a, B=b, $C_1$=r. A possible iris-sclera boundary radius $C_2$ (Eq. 2) is calculated as the mode radius of $BW_{\theta:w}$, where the mode is determined as the highest count at an integer radius, where the count at =each radius is computed as:

$$\text{count}_{\text{radius}} = \sum_{i=1}^{N} \begin{cases} 1 & \left\lfloor \sqrt{(A - x_{i:w})^2 + (B - y_{i:w})^2} \right\rfloor = \text{radius} \\ 0 & \text{otherwise} \end{cases} \qquad (41)$$

If at least one subset of black-to-white gradient points $SUBARC_{\delta:\theta:r}$ is deemed reliable, then the highest scoring subset $SUBARC_{\Delta:\theta:r}$ found such that:

$$\text{score}_{\Delta:w} \geq \text{score}_{\delta:w} \; \forall \delta = 0, 45, \ldots, 315 \qquad (42)$$

Figure 6D:
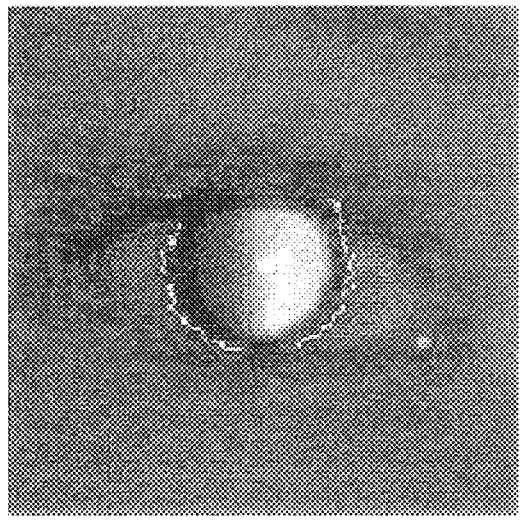
FIG. 6d is a close-up photograph of a patient's eye, showing the highest scoring subset of black-to-white gradient points from the set shown in FIG. 6c.

FIG. 6d shows the highest scoring subarc of black-to-white gradient points from the set shown in FIG. 6c. If no subset of red-to-black gradient points $SUBARC_{\delta:\theta:w}$ was deemed reliable, then the parameters (a,b,r) of the circle fitted to the points $SUBARC_{\Delta:\theta:w}$ are used to derive the parameters for an iris-sclera boundary (Eq. 2) as follows: A=a, B=b, $C_2$=r. In this case, no pupil-iris boundary is known, so the value of $C_1$ (Eq. 1) is undefined.

The overall score for the possible eye model associated with the possible corneal reflex LABEL is calculated as:

$$\text{score}_{LABEL} = \text{score}_{\Delta:r} - \text{score}_{\Delta:w} \qquad (43)$$

Note that no plausible subarc model is found for a pupil-iris circle, the first half of the overall score is 0. Although it is possible to model an eye without locating the pupil boundary, the diminished score reflects the diminished confidence in the model.

(5) Sort the eye models by strengths, and take the two best as hypothesized eyes Each hypothesized corneal reflex now has an overall model strength (i.e., likelihood of being an eye). In the next step, the set of strengths are sorted. The two strongest models are selected as the correct eye models. The correct eye models may be indicated by output from a computer, including by superimposing a graphical representation of each model on images of a corresponding eye.

More particularly, each possible corneal reflex LABEL that resulted in a possible eye model (Eq. 1–2) has an associated score (Eq. 43). The two possible eye models with the highest total score, within the following constraints, are taken to be the actual eye models, denoted as:

$$(A_{left}, B_{left}, C_{1left}, C_{2left}) \text{ and } (A_{right}, B_{right}, C_{1right}, C_{2right})$$

First, the centers of the eye models must be at least two eye diameters separated from each other:

$$\sqrt{(A_{left} - A_{right})^2 + (B_{left} - B_{right})^2} > 2(C_{2left} + C_{2right}) \quad (44)$$

Second, the orientation of the patient's face in the image is assumed to be either vertical or horizontal, but in either case level with one of the parallel sets of image boundaries. This may be verified by:

$$\arctan\left|\frac{A_{left} - A_{right}}{B_{left} - B_{right}}\right| < 30° \text{ or } \arctan\left|\frac{B_{left} - B_{right}}{A_{left} - A_{right}}\right| < 30° \quad (45)$$

The user-given orientation of the patient's face in the image (either upright, sideways-left, or sideways-right) is used to determine which model in the strongest pair corresponds to the left eye and which model corresponds to the right eye. If no pair of possible eye models passes these constraints, or fewer than two possible eye models were found, then the image is reported as being atypical and processing halts in the preferred embodiment of the invention.

(6) Measure retinal and corneal reflexes from the selected eye models, and look for abnormalities or anomalies in such reflexes In the preferred embodiment, using the best pair of possible eye models as determined above, several tests are performed to discover if any disorders of the eye are visible in the image.

Test A: In normal eyes, the corneal reflexes will be only slightly off-center (the slight offset is caused by the distance between the camera flash and the center of the camera lens). In this test, for each eye, the offset of the corneal reflex is measured as the ratio of the distance between the corneal reflex centroid and the center of the eye, to the radius of the iris:

$$\text{offset} = \frac{\sqrt{(x_c - A)^2 + (y_c - B)^2}}{C_2} \quad (46)$$

If both corneal reflexes are off-center, then the patient was not looking directly into the camera, and the computer system so indicates. If only one corneal reflex is off-center, the patient has a tropia and the computer system indicates that the patient should be referred to a medical eyecare specialist. Formally, these conditions are tested as:

$$\text{offset}_{left} > T_{cr} \text{ or } \text{offset}_{right} > T_{cr} \rightarrow \text{tropia} \quad (47)$$

$$\text{offset}_{left} > T_{cr} \text{ and } \text{offset}_{right} > T_{cr} \rightarrow \text{subject not looking} \quad (48)$$

where $T_{cr}$ is a selectable threshold.

Test B: In normal eyes, the retinal reflexes will appear equal and uniform in both eyes. To test for such uniformity, note that for each eye model (left and right) there is a corresponding pair of concentric circles modeled by (A,B, $C_1,C_2$) (Eq. 1–2), and a corneal reflex modeled by CR (Eq. 4) and its associated centroid modeled by $(x_c,y_c)$ (Eq. 8). The retinal reflex RR of each eye model preferably is measured as the average red value of pixels within the iris-pupil boundary, excluding pixels labeled as belonging to the corneal reflex and its two-deep surrounding border (the border preferably is excluded to minimize error).

Formally, let the set of pixels in the pupil to be used for computing the retinal reflex be denoted as PR, defined as:

$$PR = \text{all } (r, c) \in I \text{ such that} \quad (49)$$

$$\sqrt{(c - A)^2 + (r - B)^2} \leq C_1 \text{ and}$$

$$r \pm \{0 \ldots 2\}, c \pm \{0 \ldots 2\} \notin CR$$

The retinal reflex RR is calculated as:

$$RR = \frac{\sum_{r,c}\begin{cases}I_{red} & (r, c) \in PR \\ 0 & \text{otherwise}\end{cases}}{\sum_{r,c}\begin{cases}1 & (r, c) \in PR \\ 0 & \text{otherwise}\end{cases}} \quad (50)$$

where (r,c) denotes all pixel locations in the image. If the retinal reflexes have unequal luminance, the computer system indicates that the patient should be referred to a medical eyecare specialist. Formally, this is tested as:

$$|RR_{left} - RR_{right}| > T_{rr} \rightarrow \text{unequal luminance} \quad (51)$$

where $T_{rr}$ is a selectable threshold.

Test C: Pixels inside the pupillary boundary (excluding the corneal reflex) that are brighter than the average intensity inside the pupil are segmented into regions. Any region of sufficient size, with sufficient perimeter adjacent to the pupillary boundary, is labeled as a crescent reflex. In normal eyes, no crescent reflexes will be seen. If either eye exhibits a crescent reflex, then the patient has a refractive error and the computer system indicates that the patient should be referred to a medical eyecare specialist. Any region of sufficient size, but not adjacent to the pupillary boundary, is labeled as an abnormal pupil area (e.g. the region may represent a cataract), and the computer system indicates that the patient should be referred to a medical eyecare specialist. Note that if the pupil-iris boundary is not located for an eye, then the crescent reflex and abnormal pupil area tests are undefined in the preferred embodiment of the invention.

Formally, the average green intensity inside the pupil, denoted GR, is calculated as:

$$GR = \frac{\sum_{r,c}\begin{cases}I_{green} & (r, c) \in PR \\ 0 & \text{otherwise}\end{cases}}{\sum_{r,c}\begin{cases}1 & (r, c) \in PR \\ 0 & \text{otherwise}\end{cases}} \quad (52)$$

The average blue intensity inside the pupil, denoted BR, is calculated as:

$$BR = \left\lfloor \frac{\sum_{r,c} \begin{cases} I_{blue} & (r,c) \in PR \\ 0 & \text{otherwise} \end{cases}}{\sum_{r,c} \begin{cases} 1 & (r,c) \in PR \\ 0 & \text{otherwise} \end{cases}} \right\rfloor \quad (53)$$

An image of bright pixels inside the pupil, denoted $I_{pupil}$, is created as:

$$I_{pupil} = \begin{cases} 1 & (r,c) \in PR \text{ and} \\ & I_{red} - RR + I_{green} - GR + I_{blue} - BR \geq 70 \text{ and} \\ & (I_{red} > 200 \text{ or } I_{red} - RR > 30) \\ 0 & \text{otherwise} \end{cases} \quad (54)$$

where $I_{pupil}=1$ indicates the pixel is bright. Bright pixels are spatially grouped into four-connected regions using the queue-based paint-fill pseudocode algorithm listed above (the image I referred to in the pseudocode is in this case $I_{pupil}$). The size of each bright region is counted as the number of pixels with the same label:

$$\text{size}_{label} = \sum_{r,c} \begin{cases} 1 & I_{pupil} = \text{LABEL} \\ 0 & \text{otherwise} \end{cases} \quad (55)$$

The perimeter of each bright region is calculated as the number of bright pixels adjacent to non-bright pixels:

$$\text{perim}_{label} = \sum_{r,c} \begin{cases} 1 & I_{pupil}(r,c) = \text{LABEL and} \\ & I_{pupil}(r \pm \{0 \ldots 1\}, c \pm \{0 \ldots 1\}) = 0\} \neq 0 \\ 0 & \text{otherwise} \end{cases} \quad (56)$$

The contact of each bright region with the pupillary boundary is calculated as the number of bright pixels within a small distance of the pupil-iris circle:

$$\text{contact}_{label} = \sum_{r,c} \begin{cases} 1 & I_{pupil}(r,c) = \text{LABEL and} \\ & \left| \sqrt{(r-B)^2 + (c-A)^2} - C_1 \right| \leq 2.5 \\ 0 & \text{otherwise} \end{cases} \quad (57)$$

Bright regions are classified according to the following criteria:

$$\frac{\text{size}_{LABEL}}{2\pi C_1^2} > 0.05 \text{ and } \frac{\text{contact}_{LABEL}}{\text{perim}_{LABEL}} > 0.25 \rightarrow \text{crescent reflex} \quad (58)$$

$$\frac{\text{size}_{LABEL}}{2\pi C_1^2} > 0.05 \text{ and } \frac{\text{contact}_{LABEL}}{\text{perim}_{LABEL}} \leq 0.25 \rightarrow \text{abnormal pupil area} \quad (59)$$

$$\frac{\text{size}_{LABEL}}{2\pi C_1^2} \leq 0.05 \rightarrow \text{noise} \quad (60)$$

(7) Make a recommendation as to diagnosis

Figure 7:
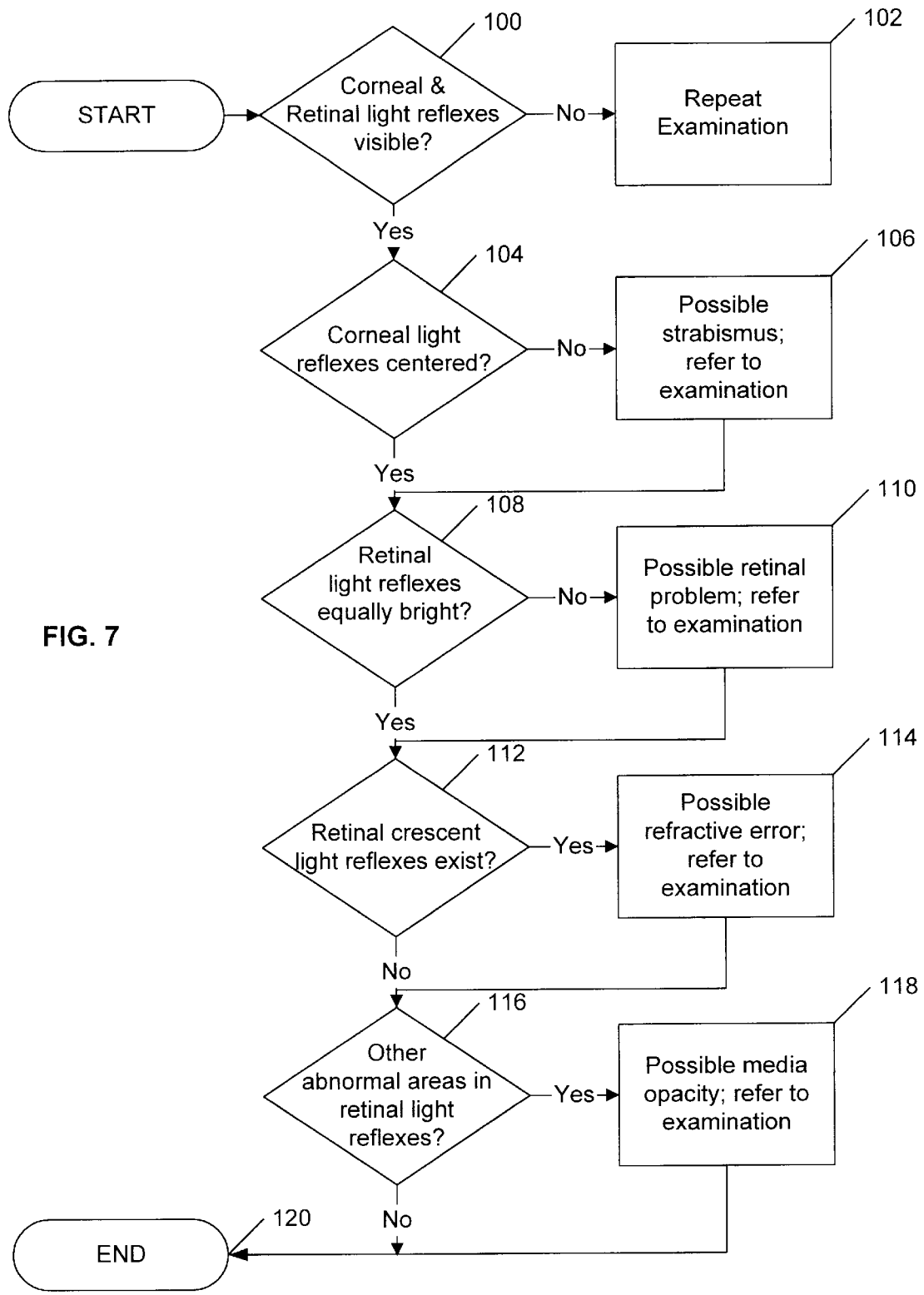
FIG. 7 is a flowchart of a preferred test sequence using the invention, once an image is acquired and the eyes are located and modeled.

FIG. 7 is a flowchart of a preferred examination sequence using the invention, once an image is acquired and the eyes are located, modeled, and analyzed. First, a determination is made as to whether the corneal and retinal light reflexes are visible in the image taken by the camera 10 (STEP 100). If not, then the examination should be repeated (i.e., another image obtained) (STEP 102). If so, then a determination is made as to whether the corneal light reflexes are centered (STEP 104). If not, then an indication is given that the patient may have strabismus, and should be referred to further examination (STEP 106). Otherwise, a determination is made as to whether the retinal (red) light reflex in both eyes is equally bright (STEP 108). If not, then an indication is given that the patient may have a retinal problem, and should be referred to further examination (STEP 110). Otherwise, a determination is made as to whether a retinal crescent light reflex exists (STEP 112). If so, then an indication is given that the patient may have a refractive error, and should be referred to further examination (STEP 114). Otherwise, a determination is made as to whether other abnormal areas exist in the retinal light reflexes (STEP 116). If so, then an indication is given that the patient may have a possible media opacity, and should be referred to further examination (STEP 118). If not, the test sequence ends (STEP 120). Note that other test sequences may also be devised, and the tests described below may be done in other orders and/or terminated after any tentative diagnosis step.

Preferred Imaging Environment

A preferred examination protocol for human patients includes (1) measuring the distance from the camera 10 to the patient; (2) centering the camera on a horizontally central landmark of the patient, preferably the patient's nose; and (3) taking an image. In addition, the inventors have determined that a preferred imaging environment for using the camera 10 of FIG. 1a includes the following practical constraints for a photographer:

- A single human patient 16 is expected, thus exactly one pair of eyes per image is expected. A parent or guardian may be holding a young child on his or her lap, so long as the image does not include the eyes of the parent or guardian.
- The patient 16 is expected to be looking directly into the camera lens 14, with both eyes open, so that the appropriate reflexes from the eyes may be imaged. Generally, for the tests to be valid, the entire pupil of each eye needs to be visible.
- The path from the camera 10 to the patient 16 should be clear of all obstacles; for instance, the patient 16 should not be wearing glasses.
- The patient 16 is expected to be directly facing the camera, photographed at a roughly known distance from the camera, using a known lens 14. This consistent configuration yields an expected range of image-apparent sizes of visual anatomical features. The constraint that the patient 16 not be too far from the camera 10 does not reflect necessarily on the ability of the inventive system to locate and model the eyes. Rather, this constraint is imposed to insure the eye regions are imaged by a sufficient number of pixels for making statistically sound measurements for making photo-screening decisions.
- The patient's eyes should be dilated. Typically, the normal dilation that occurs after three to five minutes in a darkened room is acceptable. The ambient lighting level in the room in which the picture is taken should be as dark as possible, to preserve dilation.
- Although the embodiment of the invention described herein is designed to be robust in the presence of a confusing background, the image is expected to be reasonably free of clutter. For instance, the background should not contain life-size pictures of people (particularly faces). Normal jewelry is acceptable, but anything which has an eye-like appearance should be removed.

The patient's eyes are expected to be roughly parallel with either the horizontal or vertical image boundary. Two orientations are allowed for testing for the defined visual problems.

Calibrating Algorithm Parameters

Several thresholds and parameters have been identified in the description of our algorithms which locate, model, and screen the eyes. The values for these parameters depend upon several calibration factors: the size (rows by columns, in pixels) of the digital image, the image quantization (in bits per pixel), the distance of the subject from the camera, the optical magnification of the lens (or lenses) mounted on the camera, the displacement of the flash from the center of the optical lens, and the power of the flash (in lumens). Calibration of the location of the near-axis flash was accomplished on an empirical basis. Development included compensation for a non-threatening distance from a patient. This required adjusting the flash location with respect to the optical axis of the camera lens in such a way as to maximize the image screening reflexes. Placement of the flash too close to the optical center overwhelms the response, whereas placement too far diminishes the response. Adjustment of the camera light sensor also was necessary to insure a standard number of lumens per flash.

We have successfully constructed and calibrated two working systems based upon different cameras, thereby resulting in different values for the algorithm parameters; however, conceptually, changing these values does not change how the inventive system operates. Of the two configurations tested, we chose the one with the larger image resolution, because larger numbers of samples (in this case, pixels) generally result in statistically more sound decisions. The currently preferred configuration uses a Kodak DC120 digital camera, which captures a 1280×960×24 bit (RGB) image. Subjects are photographed at a distance of about 3.5 feet (i.e., slightly over one meter). This distance helps avoid changes in the refractive characteristics of a patient's eyes due to accommodation (i.e., muscle induced changes in the curvature of the eye due to focusing on close objects), and is less intrusive to the patient.

The camera has a built-in 3× lens, to which has been attached an additional 2× lens, giving an effective 6× magnification. The flash is a standard model from Kodak Corporation, consisting of a flash tube encased in a reflector. The flash tube measures about 27.25 mm (length) by about 2.5 mm (diameter). The reflector measures about 7.8 mm (width) by about 25.1 mm (length) by about 5.5 mm (depth). The flash is placed about 17.25 mm from the optical axis (measured from the center of the reflector—which is also the center of the flash tube—to the center of the optical axis).

For this camera and flash configuration, values for the algorithm parameters described above have been calibrated as follows:

| | |
|---|---|
| $T_1 = 6$ | $T_L = 80$ |
| $T_2 = 39$ | $T_B = 200$ |
| $T_3 = 17$ | $T_\theta = 2.0$ |
| $T_4 = 83$ | $T_{rr} = 20$ |
| $T_5 = 4$ | $T_{cr} = 0.2$ |

Computer Implementation

The invention may be implemented in hardware or software, or a combination of both (e.g., programmable logic arrays). Unless otherwise specified, the algorithms included as part of the invention are not inherently related to any particular computer or other apparatus. In particular, various general purpose machines may be used with programs written in accordance with the teachings herein, or it may be more convenient to construct more specialized apparatus to perform the required method steps. However, preferably, the invention is implemented in one or more computer programs executing on programmable systems each comprising at least one processor, at least one data storage system (including volatile and non-volatile memory and/or storage elements), at least one input device, and at least one output device. Program code is applied to input data to perform the functions described herein and generate output information. The output information is applied to one or more output devices, in known fashion.

Each such program may be implemented in any desired computer language (including machine, assembly, high level procedural, or object oriented programming languages) to communicate with a computer system. In any case, the language may be a compiled or interpreted language. Each such computer program is preferably stored on a storage media or device (e.g., ROM, CD-ROM, or magnetic or optical media) readable by a general or special purpose programmable computer, for configuring and operating the computer when the storage media or device is read by the computer to perform the procedures described herein. The inventive system may also be considered to be implemented as a computer-readable storage medium, configured with a computer program, where the storage medium so configured causes a computer to operate in a specific and predefined manner to perform the functions described herein.

A number of embodiments of the present invention have been described. Nevertheless, it will be understood that various modifications may be made without departing from the spirit and scope of the invention. For example, certain of the steps described above for some of the processes are absolutely or relatively order-independent, and thus may be performed in an order other than as described. As another example, other diagnostic tests may be applied or devised that use the eye models generated by the invention. As yet another example, the inventive system and method may be used with non-human patients. Accordingly, other embodiments are within the scope of the following claims.

What is claimed is:

1. A computer implemented method for locating a patient's eyes in a digital image that includes each eye as illuminated by a near-axis flash, including the steps of automatically finding light reflexes in the digital images as indicative of the location of each eye and analyzing such light reflexes to determine at least one possible pupil border or iris-sclera border.

2. The method of claim 1, wherein the step of analyzing such light reflexes includes determining both possible pupil and iris-sclera borders.

3. The method of claim 1, further including the step of automatically fitting a corresponding model to at least one such possible pupil border or iris-sclera border.

4. The method of claim 3 further including the step of analyzing the model of each eye to determine possible abnormalities in each eye.

5. The method of claim 4, further including the step of outputting a possible diagnosis for each eye based on such analyzing.

6. A computer implemented method for modeling a patients eyes in a digital image that includes each eye as illuminated by a near-axis flash, including the step of automatically fitting a model to each eye in the digital images based on locating light reflections in the digital images as possible light reflexes from each eye and analyzing such possible light reflexes to determine at least one possible pupil border or iris-sclera border.

7. The method of claim 6, wherein the step of analyzing such possible light reflexes includes determining both possible pupil and iris-sclera borders.

8. The method of claim 6, further including the step of analyzing the model of each eye to determine possible abnormalities in each eye.

9. The method of claim 8, further including the step of outputting a possible diagnosis for each eye based on such analyzing.

10. A computer implemented method for locating and modeling a patient's eyes in a digital image that includes each eye as illuminated by a near-axis flash, including the steps of:
   (a) finding and indicating bright spots in the digital images as possible corneal reflexes of each eye;
   (b) finding and indicating red-black and black-white gradients, each comprising a set of gradient points, around such bright spots as possible pupil and iris-sclera borders, respectively, of each eye;
   (c) fitting a plurality of circles to subsets of such gradient points as possible models for each eye, each eye model having an associated strength; and
   (d) sorting the eye models for each eye by strengths, and indicating the strongest corresponding eye model as best representing each eye.

11. The method of claim 10, further including the step of measuring retinal reflexes and corneal reflexes from each indicated eye model as an indicator of possible abnormalities in each eye.

12. The method of claim 11, further including the step of outputting a possible diagnosis for each eye based on such measuring.

13. A computer implemented method for locating and modeling a patient's eyes, including the steps of:
   (a) illuminating the patient's eyes with a near-axis flash;
   (b) generating a digitized image that includes each eye;
   (c) finding and indicating bright spots in the digital image as possible corneal reflexes of each eye;
   (d) finding and indicating red-black and black-white gradients, each comprising a set of gradient points, around such bright spots as possible pupil and iris-sclera borders, respectively, of each eye;
   (e) fitting a plurality of circles to subsets of such gradient points as possible models for each eye, each eye model having an associated strength; and
   (f) sorting the eye models for each eye by strengths, and indicating the strongest corresponding eye model as best representing each eye.

14. The method of claim 13, further including the step of measuring retinal reflexes and corneal reflexes from each indicated eye model as an indicator of possible abnormalities in each eye.

15. The method of claim 14, further including the step of outputting a possible diagnosis for each eye based on such measuring.

16. The method of claims 11 or 14, wherein the step of measuring retinal reflexes and corneal reflexes from each indicated eye model as an indicator of possible abnormalities in each eye includes the steps of determining and indicating if the retinal reflexes appear equal and uniform in both eyes.

17. The method of claims 11 or 14, wherein the step of measuring retinal reflexes and corneal reflexes from each indicated eye model as an indicator of possible abnormalities in each eye includes the steps of determining and indicating if only one corneal reflex is off-center.

18. The method of claims 11 or 14, wherein the step of measuring retinal reflexes and corneal reflexes from each indicated eye model as an indicator of possible abnormalities in each eye includes the steps of determining and indicating if a crescent reflex exists in any eye.

19. The method of claims 11 or 14, wherein the step of measuring retinal reflexes and corneal reflexes from each indicated eye model as an indicator of possible abnormalities in each eye includes the steps of determining and indicating for each eye if an abnormal pupil area exists spaced from the pupillary boundary indicated by the corresponding eye model.

20. A computer implemented method for locating and modeling a patient's eyes, including the steps of:
   (a) generating a digital image of each of a patient's eyes with a camera having a flash positioned near to a center line of a lens of the camera so as to generate an image with bright, sharp light reflexes;
   (b) finding and indicating bright spots in the digital image as possible corneal reflexes of each eye;
   (c) finding and indicating red-black and black-white gradients, each comprising a set of gradient points, around such bright spots as possible pupil and iris-sclera borders, respectively, of each eye;
   (d) fitting a plurality of circles to subsets of such gradient points as possible models for each eye, each eye model having an associated strength; and
   (e) sorting the eye models for each eye by strengths, and indicating the strongest corresponding eye model as best representing each eye.

21. The method of claim 20, further including the step of measuring retinal reflexes and corneal reflexes for each indicated eye model as an indicator of possible abnormalities in each eye.

22. The method of claim 21, further including the step of outputting a possible diagnosis for each eye based on such measuring.

23. The method of claims 13 or 20, wherein the step of finding and indicating bright spots in the digital image as possible corneal reflexes includes the steps of:
   (a) spatially grouped bright pixels of each digital image into four-connected regions;
   (b) labeling such four-connected regions with areas within a selected size range as possible corneal reflexes.

24. The method of claims 23, wherein the step of finding and indicating red-black and black-white gradients includes the steps of:
   (a) determining a centroid for each possible corneal reflex;
   (b) defining a set of rays as each centroid together with pixels of the digital image along a set of compass directions from the centroid;
   (c) applying a gradient filter to a segment of each ray;
   (d) for each such segment, determining the pixel with the highest red-to-black gradient and the pixel with the highest black-to-white gradient;
wherein the set of pixels with the highest red-to-black gradient from all segments comprise a possible pupil border, and wherein the set of pixels with the highest black-to-white gradient from all segments comprise a possible iris-sclera border.

25. The method of claim 24, wherein the step of fitting a plurality of circles to subsets of such gradient points as possible eye models, includes the steps of:

(a) applying a least-squares solution to fit at least one circle equation in the form of subarcs to the gradient points comprising the possible pupil border and the gradient points comprising the possible iris-sclera border, for each possible corneal reflex; and (b) computing a circle strength score for each fit of at least one circle equation.

26. The method of claim 25, wherein the step of sorting the eye models by strengths includes the steps of:

(a) normalizing and sorting the circle strength scores for each eye;

(b) selecting the circle equation with the best circle strength score as a model for the corresponding eye.

27. A system for locating a patient's eyes and for enabling modeling of the patient's eyes and determination of the presence of anomalies in the patient's visual anatomy, including:

(a) a camera having a flash positioned near to the optical axis of a lens of the camera for generating a digital image of each of a patient's eyes with bright, sharp light reflexes; and (b) a computer programmed to automatically find the light reflexes in the digital images as indicative of the location of each eye and to analyze such light reflexes to determine at least one possible pupil border or iris-sclera border.

28. The system of claim 27, wherein the computer is farther programmed to analyze such light reflexes to determine both possible pupil and iris-sclera borders.

29. The system of claim 28, wherein the computer is further programmed to fit a corresponding model to such possible pupil and iris-sclera borders.

30. The system of claim 29, wherein the computer is further programmed to analyze the model of each eye to determine possible abnormalities in each eye.

31. The system of claim 30, wherein the computer is further programmed to output a possible diagnosis for each eye based on such analysis.

* * * * *